United States Patent [19]

Tsukii et al.

[11] Patent Number: 5,807,539
[45] Date of Patent: Sep. 15, 1998

[54] INSECTICIDAL AND ACARICIDAL SMOKE FUMIGANT COMPOSITIONS

[75] Inventors: Takeo Tsukii, Yokohama; Hiromu Akizuki, Wakayama; Mitsuyasu Makita, Nishinomiya, all of Japan

[73] Assignee: Sumitomo Chemical Company, Limited, Osaka, Japan

[21] Appl. No.: 293,202

[22] Filed: Aug. 19, 1994

[30] Foreign Application Priority Data

Aug. 20, 1993 [JP] Japan .................................. 5-206530

[51] Int. Cl.⁶ .................................................. A01N 25/12
[52] U.S. Cl. .............................. 424/40; 424/405; 424/43; 424/DIG. 10; 514/919
[58] Field of Search ........................... 424/405, DIG. 10, 424/43, 40, 42, 489; 514/919

[56] References Cited

U.S. PATENT DOCUMENTS 2,590,529  3/1952  Gillies et al. ............................. 424/40
4,228,124 10/1980  Kashihara et al. ....................... 422/36

OTHER PUBLICATIONS

Patent Abstracts of Japan, vol. 016, No. 244 (C–0947), 4 Jun. 1992.
Patent Abstracts of Japan, vol. 007, No. 252 (C–194), 9 Nov. 1983.
Patent Abstracts of Japan, Section Ch, Week 7951, Derwent Publications Ltd., London, GB.

*Primary Examiner*—Raj Bawa
*Attorney, Agent, or Firm*—Sughrue, Mion, Zinn, Macpeak & Seas, PLLC

[57] ABSTRACT

An insecticidal and acaricidal smoke fumigant formulation obtained by mixing granules A having a bulk specific gravity of 0.3 to 0.9 and containing a pyrethroid compound as an active ingredient, an inflammable substance and an organic blowing agent, with granules B having a bulk specific gravity of 0.5 to 1.1 and containing potassium perchlorate, potassium nitrate and/or potassium chlorate, burning agent, heat generation-regulating agent, perchlorate-decomposing aid and inorganic filler, the mixing ratio (weight ratio) of the granules A and the granules B being 1 to 0.5–4.

34 Claims, 1 Drawing Sheet

INSECTICIDAL AND ACARICIDAL SMOKE FUMIGANT COMPOSITIONS

FIELD OF THE INVENTION

The present invention relates to an insecticidal and acaricidal smoke fumigant formulation, which is particularly useful for indoor uses.

BACKGROUND OF THE INVENTION

For many years, mosquito coils and electric mosquito mats have widely been used to exterminate mosquitos, but they are not effective against bedbugs, house ticks (*Ornithonyssus bacoti*), cockroaches.

For extermination of bedbugs, house ticks, cockroaches, etc., jet-type smoke fumigant formulations have been developed.

In conventional jet-type smoke fumigant formulations, an active ingredient—which is mixed with a smoking agent—is jetted by the ignition of the smoking agent. The conventional jet-type smoke fumigant formulations do not exert sufficient insecticidal effects of the active ingredient because a considerable amount of the active ingredient contained in the jet-type smoke fumigant formulations is decomposed by the heat generated from the combustion of the smoking agent, and because the combustion temperature of the formulations is controlled to rather low from the standpoint of safety, and, hence, so is the vaporizing rate of the active ingredient.

Accordingly, there has been a strong demand for the development of smoke fumigant formulations, which can safely be burned to release the active ingredient at a high vaporizing rate, thereby exerting a potent insecticidal and acaricidal effects against bedbugs, house ticks, cockroaches, etc.

SUMMARY OF THE INVENTION

In order to develop much more effective and safe insecticidal and acaricidal smoke fumigant formulations, the present inventors have extensively studied, and, as a result, invented an insecticidal and acaricidal smoke fumigant formulation, which comprises: (A) 1 part by weight of granules A comprising 5 to 20 parts by weight of at least one pyrethroid compound as an active ingredient; 10 to 20 parts by weight of at least one inflammable substance selected from the group consisting of celluloid and polyvinyl nitrate; and 5 to 50 parts by weight of at least one organic blowing agent selected from the group consisting of azodicarbonamide, dinitrosopentamethylenetetramine and azobisisobutyronitrile, the bulk specific gravity of the granules A being 0.3 to 0.9, preferably 0.3 to 0.6; and (B) 0.5 to 4 parts by weight, preferably 1 to 3 parts by weight, of granules B comprising 10 to 20 parts by weight of potassium perchlorate, 3 to 8 parts by weight of potassium nitrate and/or 1 to 5 parts by weight of potassium chlorate, 7 to 20 parts by weight of at least one burning agent selected from the group consisting of starch, lactose, cellulose, sucrose, glucose, fructose and mannitol, 3 to 8 parts by weight of at least one heat generation-regulating agents selected from the group consisting of guanidine nitrate, dicyandiamide, phosphoric guanylurea and guanidine sulfamate, 15 to 30 parts by weight of at least one perchlorate-decomposing aid selected from the group consisting of potassium chloride, triiron tetroxide, sodium chloride, copper oxide, chromium oxide, iron oxide, iron chloride, active carbon and ferrocene and 20 to 50 parts by weight of at least one inorganic filler selected from the group consisting of aluminum oxide, clay, perlite, diatomaceous earth and talc, the bulk specific gravity of the granules B being 0.5 to 1.1, preferably 0.6 to 1.0.

The insecticidal and acaricidal smoke fumigant formulations of the present invention have advantages that the active ingredient is very effectively vaporized, with little decomposition, by the combustion of the formulation, and exerts a strong insecticidal and acaricidal effect against said pests, and that they can safely be used indoors since their combustion is relatively mild and the combustion temperature is relatively low.

DETAILED DESCRIPTION OF THE INVENTION

The present invention will be illustrated below.

The pyrethroid compounds which may be used in the insecticidal and acaricidal smoke fumigant formulation of the present invention include, for example, cyphenothrin [(RS)-α-cyano-3-phenoxybenzyl (1R)-cis,trans-chrysanthemate], allethrin [(RS)-3-allyl-2-methyl-4-oxocyclopent-2-enyl (1RS)-cis,trans-chrysanthemate], prallethrin [(S)-2-methyl-4-oxo-3-(2-propynyl)cyclopent-2-enyl (1R)-cis,trans-chrysanthemate], tetramethrin [N-(3,4,5,6-tetrahydrophthalimidomethyl (1RS)-cis,trans-chrysanthemate], resmethrin [5-benzyl-3-furylmethyl (1RS)-cis,trans-chrysanthemate], d-phenothrin [3-phenoxybenzyl (1R)-cis,trans-chrysanthemate], permethrin [3-phenoxybenzyl (1RS)-cis,trans-3-(2,2-dichlorovinyl)-2,2-dimethylcyclopropanecarboxylate], fenvalerate [(RS)-α-cyano-3-phenoxybenzyl (RS)-2-(4-chlorophenyl)-3-methylbutyrate], fenpropathrin [(RS)-α-cyano-3-phenoxybenzyl 2,2,3,3-tetramethylcyclopropanecarboxylate], trans-fluthrin (benfluthrin) [2,3,5,6-tetrafluorobenzyl (1R)-trans-3-(2,2-dichlorovinyl)-2,2-dimethylcyclopropanecarboxylate], cypermethrin [(RS)-α-cyano-3-phenoxybenzyl (1RS)-cis,trans-3-(2,2-dichlorovinyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], optical isomers and stereoisomers of these compounds and mixtures thereof.

In the granules A described above, the mixing ratio of the pyrethroid compound as an active ingredient and the inflammable substance is preferably 1 to 0.8–2 (weight ratio).

The celluloid used as the inflammable substance for the granules A include the celluloid itself and solid solutions of nitrocellulose with plasticizers such as tricresyl phosphate, dibutyl phthalate and tributyl acetylcitrate. It is preferred that the granules A contain further components, i.e. a celluloid-stabilizing agent and a heat generation-regulating agent. The amount of the former agent is 0.1 to 5 parts by weight of at least one diphenylamine, ethyl centralit, methyl centralit and 2-nitrodiphenylamine, and the amount of the latter agent is 3 to 15 parts by weight of at least one guanidine nitrate, dicyandiamide and nitroguanidine.

If necessary, the granules A may further contain 1 to 50 parts by weight of at least one inorganic filler such a aluminum oxide, clay, talc, diatomaceous earth and perlite and 3 to 15 parts by weight of at least one blowing-regulating agents such as zinc oxide and calcium stearate. Further, the granules A may contain antioxidants (e.g. BHT), efficacy enhancer (e.g. piperonyl butoxide, MGK-264, S-421, etc.), perfumes and deodorants.

In producing the granules A, usually, the predetermined amounts of the above components and a suitable amount of water or a lower alcohol (e.g. methyl alcohol) are mixed and kneaded together, and the resulting mixture may be granulated into granules and dried according to a usual method to obtain the desired granules A. In order to facilitate granulation, it is preferred to add 0.1 to 4 parts by weight, more preferably 0.5 to 3 parts by weight of a thickening agent (e.g. methyl cellulose, hydroxypropylmethyl cellulose) as a granulation aid.

The particle size of the granules A thus obtained is usually 0.5 to 3.5 mm, preferably 1.0 to 2.5 mm.

The granules B described above may contain 0.1 to 4 parts by weight, preferably 0.5 to 3 parts by weight of a thickening agent (e.g. methyl cellulose, hydroxypropylmethyl cellulose) as a granulation aid. In producing the granules B, usually, the predetermined amount of the above components and a suitable amount of water are mixed and kneaded together, and the resulting mixture is granulated into granules and then dried the granules according to the usual method.

The particle size of the granules B thus obtained is usually 0.5 to 3.5 mm, preferably 1.0 to 2.5 mm.

The smoke fumigant formulations of the present invention are usually prepared by packing each or a mixture of the thus obtained granules A and B into a container (e.g., paper cylinder), and then setting an igniting agent such as a formed thermit.

By igniting the smoke fumigant formulation of the present invention, the vapor of the active ingredient is efficiently spread in a moment in a large space. Thus, the formulation of the present invention can effectively exterminate not only mosquitos or flies but also insanitary pests such as bedbugs, house ticks, or cockroaches hiding behind or under furnitures or other things. Moreover, from the standpoint of possibility of causing fires, the smoke fumigant formulation of the present invention is safe and, hence, particularly suited for indoor uses.

The present invention will be illustrated more specifically with reference to the following examples and comparative examples, but it is not to be interpreted as being limited to these examples.

In each example, all parts mean a part by weight.

EXAMPLE 1

The granules A having a bulk specific gravity of 0.4 was obtained by mixing 15 parts of cyphenothrin, 17 parts of celluloid, 28 parts of azodicarbonamide, 0.4 part of diphenylamine (hereinafter referred to as DPA), 29.1 parts of perlite and 10 parts of zinc oxide, kneading and mixing the resulting mixture with 0.5 part of methyl cellulose and a suitable amount of water, granulating the resulting mixture according to a usual method, and then drying the granules.

The granules B having a bulk specific gravity of 0.92 were obtained by mixing 10 parts of potassium perchlorate, 3 parts of potassium chlorate, 10 parts of lactose, 6 parts of guanidine nitrate, 10 parts of potassium chloride, 15 parts of triiron tetroxide, 20 parts of aluminum oxide and 25 parts of kaolin clay, kneading and mixing the resulting mixture with 1 part of methyl cellulose and a suitable amount of water, granulating the resulting mixture according to the usual method, and then drying the granules.

A smoke fumigant formulation was obtained by putting 10.0 g of the granules A obtained above in a cylindrical paper container (diameter 36 mm; height 80 mm), laying a glass wool net on the granules A and then putting 15.0 g of the granules B on the net. The vaporizing rate of the active ingredient (cyphenothrin) of the resulting smoke fumigant formulation was measured according to the following method to find that it was 78%.

Method for Measuring Vaporizing Rate of the Active Ingredient

In measuring the vaporizing rate, an instrument shown in FIG. 1 was used. One hundred grams of silica gel is packed in a glass filter 3 and the lower part of the glass filter is connected to a suction pump.

The ignited smoke fumigant formulation was immediately placed on a wire net 2a in the body 2 of a container, and the body was covered with a covering container 1. An air-drawing cock 4 is opened, and the generated smoke was suctioned at a rate of 25 ml/min. from the lower part of the glass filter.

After thirty seconds from the completion of fuming of the smoke fumigant formulation, suction was stopped. The insides of the covering container 1, the body 2 of the container and the glass filter 3 were washed with acetone, and the washings and an acetone extract obtained by extracting the silica gel in the glass filter 3 with acetone were combined. The amount of the collected active ingredient contained in the combined acetone solution was measured by gas chromatography, and the vaporizing rate of the active ingredient was calculated according to the following equation:

$$\text{vaporizing rate (\%)} = \frac{\text{amount of the collected active ingredient}}{\text{amount of the active ingredient in the smoke fumigant formulation}} \times 100$$

EXAMPLE 2

The granules A having a bulk specific gravity of 0.34 were obtained by mixing 15 parts of cyphenothrin, 19 parts of celluloid, 32 parts of azodicarbonamide, 0.4 part of DPA, 23.1 parts of perlite and 10 parts of zinc oxide, kneading and mixing the resulting mixture with 0.5 part of methyl cellulose and a suitable amount of water, granulating the resulting mixture according to a usual method, and then drying the granules.

The granules B having a bulk specific gravity of 0.8 were obtained by mixing 10 parts of potassium perchlorate, 3 parts of potassium chlorate, 10 parts of lactose, 6 parts of guanidine nitrate, 10 parts of potassium chloride, 15 parts of triiron tetroxide, 20 parts of aluminum oxide and 25 parts of kaolin clay, kneading and mixing the resulting mixture with 1 part of methyl cellulose and a suitable amount of water, granulating the resulting mixture according to a usual method, and then drying the granules.

In the same manner as in Example 1, the smoke fumigant formulation was obtained by packing a cylindrical paper container with 10.5 g of the granules A and 16.0 g of the granules B, both of which were obtained above. The vaporizing rate of the cyphenothrin of this smoke fumigant formulation was measured by the same method as used in Example 1 to find that it was 70%.

EXAMPLE 3

The granules A having a bulk specific gravity of 0.31 were obtained by mixing 20 parts of cyphenothrin, 19 parts of celluloid, 32 parts of azodicarbonamide, 0.4 part of DPA, 18.1 parts of perlite and 10 parts of zinc oxide, kneading and mixing the resulting mixture with 0.5 part of methyl cellulose and a suitable amount of water, granulating the resulting mixture according to a usual method, and then drying the granules.

The granules B having a bulk specific gravity of 0.8 were obtained by mixing 10 parts of potassium perchlorate, 3 parts of potassium chlorate, 10 parts of lactose, 6 parts of guanidine nitrate, 10 parts of potassium chloride, 15 parts of triiron tetroxide, 20 parts of aluminum oxide and 25 parts of kaolin clay, kneading and mixing the resulting mixture with 1 part of methyl cellulose and a suitable amount of water, granulating the resulting mixture according to a usual method, and then drying the granules.

In the same manner as in Example 1, the smoke fumigant formulation was obtained by packing a cylindrical paper container with 10.5 g of the granules A and 16.0 g of the granules B, both of which were obtained as above. The vaporizing rate of cyphenothrin of this smoke fumigant formulation was measured by the same method as used in Example 1 to find that it was 75%.

COMPARATIVE EXAMPLE 1

The granules A having a bulk specific gravity of 0.32 were obtained according to Example 1. The granules B having a bulk specific gravity of 0.7 were obtained by mixing 17.5 parts of celluloid, 18 parts of guanidine nitrate, 5 parts of copper oxide, 5 parts of dicyandiamide and 53.5 parts of kaolin clay, kneading and mixing the resulting mixture with 1 part of methyl cellulose and a suitable amount of water, granulating the resulting mixture according to a usual method, and then drying the granules.

In the same manner as in Example 1, the smoke fumigant formulation for comparison was obtained by packing a cylindrical paper container with 11.0 g of the granules A and 16.0 g of the granules B, both of which were obtained above. In this case, the granules B do not contain potassium perchlorate, potassium nitrate or potassium chlorate and a particular burning agent unlike the smoke fumigant formulation of the present invention. The vaporizing rate of cyphenothrin of this smoke fumigant formulation was measured by the same method as used in Example 1 to find that it was 46%.

COMPARATIVE EXAMPLE 2

The granules A having a bulk specific gravity of 0.3 were obtained by mixing 20 parts of cyphenothrin, 75 parts of azodicarbonamide and 4 parts of zinc oxide, kneading and mixing the resulting mixture with 1 part of hydroxypropylmethyl cellulose and a suitable amount of water, granulating the resulting mixture according to a usual method, and then drying the granules. The granules B having a bulk specific gravity of 0.8 were obtained according to Example 1. The smoke fumigant formulation for comparison was obtained by mixing 10.5 g of the granules A and 16.0 g of the granules B, both of which were obtained above, and packing a cylindrical paper container (diameter 33 mm, height, 50 mm) with the resulting mixture. In this case, the granules A do not contain the particular inflammable substance unlike the smoke fumigant formulation of the present invention. The vaporizing rate of cyphenothrin of this comparative smoke fumigant formulation was measured by the same method as used in Example 1 to find that it was 38%.

EXAMPLE 4

The smoke fumigant formulations were obtained by mixing 11.3 g of each of the granules A having a bulk specific gravity of from 0.32 to 0.65 and 16.0 g of the granules B having a bulk specific gravity of 0.9, all of which were produced according to Example 1, and packing a cylindrical paper container (diameter 33 mm, height 50 mm) with the resulting mixture. The vaporizing rate of cyphenothrin of these smoke fumigant formulations was measured by the same method as used in Example 1. The results are shown in Table 1.

TABLE 1

| Bulk specific gravity of the granules A | Bulk specific gravity of the granules B | Vaporizing rate (%) |
| --- | --- | --- |
| 0.32 | 0.90 | 70.1 |
| 0.33 | 0.90 | 73.0 |
| 0.40 | 0.90 | 71.0 |
| 0.50 | 0.90 | 65.0 |
| 0.65 | 0.90 | 60.0 |

EXAMPLE 5

The smoke fumigant formulations were obtained by mixing 15.0 g of each of the granules B having a bulk specific gravity of from 0.6 to 1.0 and 11.0 g of the granules A having a bulk specific gravity of 0.4, all of which were produced according to Example 1, and packing a cylindrical paper container (diameter 33 mm, height 50 mm) with the resulting mixture. The vaporizing rate of cyphenothrin of these smoke fumigant formulations was measured by the same method as used in Example 1. The results are shown in Table 2.

TABLE 2

| Bulk specific gravity of the granules A | Bulk specific gravity of the granules B | Vaporizing rate (%) |
| --- | --- | --- |
| 0.40 | 0.60 | 61.8 |
| 0.40 | 0.77 | 63.0 |
| 0.40 | 0.82 | 67.3 |
| 0.40 | 0.90 | 73.0 |
| 0.40 | 1.00 | 70.0 |

EXAMPLE 6

11.3 g of the granules A having a bulk specific gravity of 0.4 and the varying amounts described in Table 2 of the granules B having a bulk specific gravity of 0.9, all of which were produced according to Example 1, were mixed in the weight ratio of from 1:0.8 to 1:3.5. Thereafter, the smoke fumigant formulations were produced by packing cylindrical paper containers (diameter 33 m) with the mixture obtained above. The vaporizing rates of cyphenothrin of these smoke fumigant formulations were measured by the same method as used in Example 1. The results are shown in Table 3.

TABLE 3

| Granules A | Granules B | A:B (weight ratio) | Height of cylindrical paper container (mm) | Vaporizing rate (%) |
| --- | --- | --- | --- | --- |
| 11.3 g | 9.0 g | 1:0.8 | 50 | 50.1 |
| 11.3 g | 11.3 g | 1:1 | 50 | 53.4 |
| 11.3 g | 17.0 g | 1:1.5 | 50 | 66.8 |
| 11.3 g | 22.6 g | 1:2.0 | 50 | 64.5 |
| 11.3 g | 28.3 g | 1:2.5 | 70 | 58.5 |
| 11.3 g | 33.9 g | 1:3.0 | 70 | 54.1 |
| 11.3 g | 39.6 g | 1:3.5 | 70 | 51.7 |

An example of an insecticidal test using the smoke fumigant formulation of the present invention will be shown below.

EXAMPLE 7

In a large chamber which is a rectangular parallelepiped having a floor area of 300 cm×400 cm and a height of 230 cm were put two plastic cups 10 which contained 10 German cockroaches (*Blattella germanica*) and two plastic cups 11 which contained 5 American cockroaches (*Periplaneta americana*) as shown in FIG. 2. Separately, a corrugated cardboard box 12 of 30 cm×30 cm×30 cm was prepared, and a slit of 5 mm×10 cm was made at each central part of four sides of the box so that it was parallel to the floor. The box was then set on the floor of the chamber. Further, one plastic cup containing 10 German cockroaches and one plastic cup containing 5 American cockroaches were also put in this corrugated cardboard box. The smoke fumigant formulation obtained in Example 1 was ignited and put on the center 13 of the floor of the chamber, and the inside of the large chamber was smoke fumigated. After 3 hours, the cockroaches were taken out of each plastic cup and transferred to a clean container containing bait and water. After 3 days, the condition, dead or alive, of the cockroaches were observed.

As a result, it was found that the mortality of the test cockroaches was 100%.

That is, the cockroaches could be effectively controlled because the generated smoke fumigant entered the corrugated cardboard box even through the slits made in the box.

Figure 1:
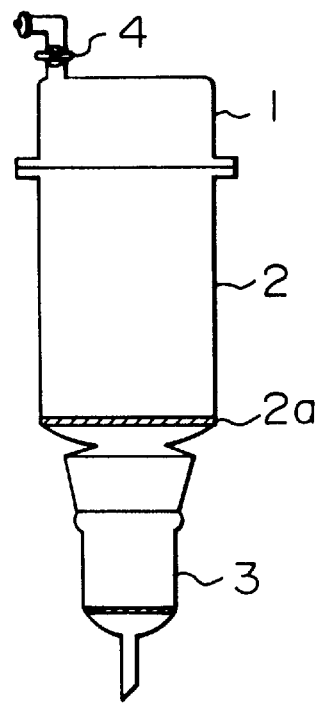
FIG. 1 is a sectional view of the instrument used to measure the vaporizing rate of the smoke fumigant formulations of the present invention in Examples 1 to 6 and Comparative Examples 1 and 2.
Figure 2:
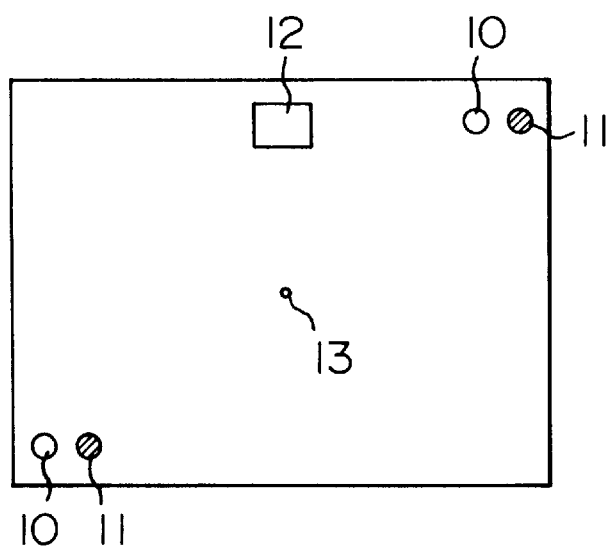
FIG. 2 is an illustrative view of the large chamber used to confirm the cockroach-controlling effect in Example 7.

1. Covering container
2. Body of the container
2a. Wire net
3. Glass filter
4. Air-drawing cock
10. Plastic cup containing German cockroaches
11. Plastic cup containing American cockroaches
12. Corrugated cardboard box
13. Position at which the smoke fumigant formulation was set.

What is claimed is:

1. An insecticidal and acaricidal smoke fumigant formulation consisting essentially of granules A having a bulk specific gravity of 0.3 to 0.9 and granules B having a bulk specific gravity of 0.5 to 1.1, said granules A comprising 5 to 20 parts by weight of at least one pyrethroid compound as an active ingredient, 10 to 20 parts by weight of at least one inflammable substance selected from the group consisting of celluloid and polyvinyl nitrate, 5 to 50 parts by weight of at least one organic blowing agent selected from the group consisting of azodicarbonamide, dinitrosopentamethylenetetramine and azobisisobutyronitrile, 0.1 to 5 parts by weight of at least one celluloid stabilizing agent selected from the group consisting of diphenylamine, ethyl centralit, methyl centralit and 2-nitrodiphenylamine, and 0.1 to 4 parts by weight of at least one granulation aid selected from the group consisting of methyl cellulose and hydroxypropylmethyl cellulose; and said granules B comprising 10 to 20 parts by weight of potassium perchlorate, 3 to 8 parts by weight of potassium perchlorate, 3 to 8 parts by weight of potassium nitrate and/or 1 to 5 parts by weight of potassium chlorate, 7 to 20 parts by weight of at least one burning agent selected from the group consisting of starch, lactose, cellulose, sucrose, glucose, fructose and mannitol, 3 to 8 parts by weight of at least one heat generation-regulating agent selected from the group consisting of guanidine nitrate, dicyandiamide, phosphoric guanylurea and guanidine sulfamate, 15 to 30 parts by weight of at least one perchlorate-decomposing aid selected from the group consisting of potassium chloride, triiron tetroxide, sodium chloride, copper oxide, chromium oxide, iron oxide, iron chloride, active carbon and ferrocene, 20 to 50 parts by weight of at least one inorganic filler selected from the group consisting of aluminum oxide, clay, perlite, diatomaceous earth and talc, and 0.1 to 4 parts by weight of at least one granulation aid selected from the group consisting of methyl cellulose and hydroxypropylmethyl cellulose;

wherein the mixing ratio (weight ratio) of the granules A and the granules B is 1 to 0.5–4.

2. An insecticidal and acaricidal smoke fumigant formulation consisting essentially of granules A having a bulk specific gravity of 0.3 to 0.9 and granules B having a bulk specific gravity of 0.5 to 1.1, said granules A comprising 5 to 20 parts by weight of at least one pyrethroid compound as an active ingredient, 10 to 20 parts by weight of at least one inflammable substance selected from the group consisting of celluloid and polyvinyl nitrate, 5 to 50 parts by weight of at least one organic blowing agent selected from the group consisting of azodicarbonamide, dinitrosopentamethylenetetramine and azobisisobutyronitrile, 0.1 to 5 parts by weight of at least one celluloid stabilizing agent selected from the group consisting of diphenylamine, ethyl centralit, methyl centralit and 2-nitrodiphenylamine, 3 to 15 parts by weight of at least one heat generation-regulating agent selected from the group consisting of guanidine nitrate, dicyandiamide and nitroguanidine, and 0.1 to 4 parts by weight of at least one granulation aid selected from the group consisting of methyl cellulose and hydroxypropylmethyl cellulose; and said granules B comprising 10 to 20 parts by weight of potassium perchlorate, 3 to 8 parts by weight of potassium perchlorate, 3 to 8 parts by weight of potassium nitrate and/or 1 to 5 parts by weight of potassium chlorate, 7 to 20 parts by weight of at least one burning agent selected from the group consisting of starch, lactose, cellulose, sucrose, glucose, fructose and mannitol, 3 to 8 parts by weight of at least one heat generation-regulating agent selected from the group consisting of guanidine nitrate, dicyandiamide, phosphoric guanylurea and guanidine sulfamate, 15 to 30 parts by weight of at least one perchlorate-decomposing aid selected from the group consisting of potassium chloride, triiron tetroxide, sodium chloride, copper oxide, chromium oxide, iron oxide, iron chloride, active carbon and ferrocene, 20 to 50 parts by weight of at least one inorganic filler selected from the group consisting of aluminum oxide, clay, perlite, diatomaceous earth and talc, and 0.1 to 4 parts by weight of at least one granulation aid selected from the group consisting of methyl cellulose and hydroxypropylmethyl cellulose;

wherein the mixing ratio (weight ratio) of the granules A and the granules B is 1 to 0.5–4.

3. An insecticidal and acaricidal smoke fumigant formulation according to claim 1, wherein the bulk specific gravity of the granules A is 0.3 to 0.6.

4. An insecticidal and acaricidal smoke fumigant formulation according to claim 2, wherein the bulk specific gravity of the granules A is 0.3 to 0.6.

5. An insecticidal and acaricidal smoke fumigant formulation according to claim 1, wherein the bulk specific gravity of the granules B is 0.6 to 1.0.

6. An insecticidal and acaricidal smoke fumigant formulation according to claim 2, wherein the bulk specific gravity of the granules B is 0.6 to 1.0.

7. An insecticidal and acaricidal smoke fumigant formulation according to claim 3, wherein the bulk specific gravity of the granules B is 0.6 to 1.0.

8. An insecticidal and acaricidal smoke fumigant formulation according to claim 4, wherein the bulk specific gravity of the granules B is 0.6 to 1.0.

9. An insecticidal and acaricidal smoke fumigant formulation according to claim 1, wherein the mixing ratio (weight ratio) of the granules A and the granules B is 1 to 1–3.

10. An insecticidal and acaricidal smoke fumigant formulation according to claim 2, wherein the mixing ratio (weight ratio) of the granules A and the granules B is 1 to 1–3.

11. An insecticidal and acaricidal smoke fumigant formulation according to claim 3, wherein the mixing ratio (weight ratio) of the granules A and the granules B is 1 to 1–3.

12. An insecticidal and acaricidal smoke fumigant formulation according to claim 4, wherein the mixing ratio (weight ratio) of the granules A and the granules B is 1 to 1–3.

13. An insecticidal and acaricidal smoke fumigant formulation according to claim 5, wherein the mixing ratio (weight ratio) of the granules A and the granules B is 1 to 1–3.

14. An insecticidal and acaricidal smoke fumigant formulation according to claim 6, wherein the mixing ratio (weight ratio) of the granules A and the granules B is 1 to 1–3.

15. An insecticidal and acaricidal smoke fumigant formulation according to claim 7, wherein the mixing ratio (weight ratio) of the granules A and the granules B is 1 to 1–3.

16. An insecticidal and acaricidal smoke fumigant formulation according to claim 8, wherein the mixing ratio (weight ratio) of the granules A and the granules B is 1 to 1–3.

17. An insecticidal and acaricidal smoke fumigant formulation according to claim 1, wherein the mixing ratio (weight ratio) of the pyrethroid compound and the inflammable substance in the granules A is 1 to 1–2.

18. An insecticidal and acaricidal smoke fumigant formulation according to claim 2, wherein the mixing ratio (weight ratio) of the pyrethroid compound and the inflammable substance in the granules A is 1 to 1–2.

19. An insecticidal and acaricidal smoke fumigant formulation according to claim 3, wherein the mixing ratio (weight ratio) of the pyrethroid compound and the inflammable substance in the granules A is 1 to 1–2.

20. An insecticidal and acaricidal smoke fumigant formulation according to claim 4, wherein the mixing ratio (weight ratio) of the pyrethroid compound and the inflammable substance in the granules A is 1 to 1–2.

21. An insecticidal and acaricidal smoke fumigant formulation according to claim 5, wherein the mixing ratio (weight ratio) of the pyrethroid compound and the inflammable substance in the granules A is 1 to 1–2.

22. An insecticidal and acaricidal smoke fumigant formulation according to claim 6, wherein the mixing ratio (weight ratio) of the pyrethroid compound and the inflammable substance in the granules A is 1 to 1–2.

23. An insecticidal and acaricidal smoke fumigant formulation according to claim 7, wherein the mixing ratio (weight ratio) of the pyrethroid compound and the inflammable substance in the granules A is 1 to 1–2.

24. An insecticidal and acaricidal smoke fumigant formulation according to claim 8, wherein the mixing ratio (weight ratio) of the pyrethroid compound and the inflammable substance in the granules A is 1 to 1–2.

25. An insecticidal and acaricidal smoke fumigant formulation according to claim 9, wherein the mixing ratio (weight ratio) of the pyrethroid compound and the inflammable substance in the granules A is 1 to 1–2.

26. An insecticidal and acaricidal smoke fumigant formulation according to claim 10, wherein the mixing ratio (weight ratio) of the pyrethroid compound and the inflammable substance in the granules A is 1 to 1–2.

27. An insecticidal and acaricidal smoke fumigant formulation according to claim 11, wherein the mixing ratio (weight ratio) of the pyrethroid compound and the inflammable substance in the granules A is 1 to 1–2.

28. An insecticidal and acaricidal smoke fumigant formulation according to claim 12, wherein the mixing ratio (weight ratio) of the pyrethroid compound and the inflammable substance in the granules A is 1 to 1–2.

29. An insecticidal and acaricidal smoke fumigant formulation according to claim 13, wherein the mixing ratio (weight ratio) of the pyrethroid compound and the inflammable substance in the granules A is 1 to 1–2.

30. An insecticidal and acaricidal smoke fumigant formulation according to claim 14, wherein the mixing ratio (weight ratio) of the pyrethroid compound and the inflammable substance in the granules A is 1 to 1–2.

31. An insecticidal and acaricidal smoke fumigant formulation according to claim 15, wherein the mixing ratio (weight ratio) of the pyrethroid compound and the inflammable substance in the granules A is 1 to 1–2.

32. An insecticidal and acaricidal smoke fumigant formulation according to claim 16, wherein the mixing ratio (weight ratio) of the pyrethroid compound and the inflammable substance in the granules A is 1 to 1–2.

33. An insecticidal and acaricidal smoke fumigant formulation according to any one of claims 1 to 32, wherein the pyrethroid compound is cyphenothrin, allethrin, prallethrin, tetramethrin, resmethrin or d-phenothrin.

34. An insecticidal and acaricidal smoke fumigant formulation according to any one of claims 1 to 32, wherein the pyrethroid compound is cyphenothrin or d-phenothrin.

* * * * *